United States Patent
Assaad

(12) 
(10) Patent No.: US 7,887,853 B1
(45) Date of Patent: Feb. 15, 2011

(54) HAND AND BODY CREAM

(76) Inventor: Phoebe Assaad, 18 Bryant Rd., Framingham, MA (US) 01701-4425

( * ) Notice: Subject to any disclaimer, the term of this patent is extended or adjusted under 35 U.S.C. 154(b) by 994 days.

(21) Appl. No.: 11/687,216

(22) Filed: Mar. 16, 2007

(51) Int. Cl.
- A61K 36/00 (2006.01)
- A61K 36/736 (2006.01)
- A61K 36/63 (2006.01)
- A61K 36/53 (2006.01)
- A61K 36/534 (2006.01)

(52) U.S. Cl. ...................... 424/725; 424/747

(58) Field of Classification Search ........................ None
See application file for complete search history.

(56) References Cited

U.S. PATENT DOCUMENTS

| | | |
|---|---|---|
| 4,707,354 A | 11/1987 | Garlen et al. |
| 5,882,657 A | 3/1999 | Miguel-Colombel et al. |
| 5,945,409 A | 8/1999 | Crandall |
| 5,997,889 A | 12/1999 | Durr et al. |
| 6,193,987 B1 | 2/2001 | Harbeck |
| 6,258,588 B1 * | 7/2001 | Demetropoulos et al. 435/257.1 |
| 6,348,352 B1 | 2/2002 | Shepard et al. |
| 6,572,868 B1 * | 6/2003 | Cope .......................... 424/400 |
| 7,101,536 B2 * | 9/2006 | Mongiat et al. ................ 424/59 |
| 2006/0210523 A1 * | 9/2006 | Majmudar .................... 424/74 |
| 2008/0175805 A1 * | 7/2008 | Schlemer ..................... 424/63 |

FOREIGN PATENT DOCUMENTS

| | | | |
|---|---|---|---|
| JP | 2001139419 A | * | 5/2001 |
| KR | 2006091355 A | * | 8/2006 |

* cited by examiner

*Primary Examiner*—Qiuwen Mi

(57) ABSTRACT

This patent discloses a hand and body skincare cream composition. The composition may include organic cocoa butter, organic sweet almond oil, and organic olive oil in volumes that substantially may be equal to each other. The composition also may include organic rosemary essential oil in a volume that substantially may be equal to a volume combination of an organic peppermint essential oil and an organic rosemary essential oil. The composition additional may include extracts that may be drawn from equal parts by weight of wild harvested Irish moss, wild harvested bladder wrack, organic dulse flakes, and organic green rooibos tea.

4 Claims, 1 Drawing Sheet

HAND AND BODY CREAM

BACKGROUND

1. Field

The information disclosed in this patent relates to a cream that may be used on a person's hands and body to moisturize and revitalize skin.

2. Background Information

Cosmetics may be thought of as products intended to be applied to the human body for cleansing, beautifying, promoting attractiveness, or altering the appearance without affecting the body's structure or functions. Cosmetics may include substances used to enhance or protect the appearance or odor of the human body. Cosmetics include skincare creams, lotions, powders, perfumes, lipsticks, fingernail polishes, eye and facial makeup, permanent waves, hair colors, deodorants, baby products, bath oils, bubble baths, and many other types of products.

Skincare creams include creams that may clean, creams that may exfoliate, creams that moisturize, and a combination thereof. Many creams use products that are not natural, which may raise concerns with some consumers. Human skin also needs nutrients that many skincare creams fail to supply. What is needed is a hand and body cream for the skin to overcome these and other problems.

SUMMARY

This patent discloses a hand and body skincare cream composition. The composition may include organic cocoa butter, organic sweet almond oil, and organic olive oil in volumes that substantially may be equal to each other. The composition also may include organic rosemary essential oil in a volume that substantially may be equal to a volume combination of an organic peppermint essential oil and an organic rosemary essential oil. The composition additional may include extracts that may be drawn from equal parts by weight of wild harvested Irish moss, wild harvested bladder wrack, organic dulse flakes, and organic green rooibos tea.

DETAILED DESCRIPTION

Figure 1:
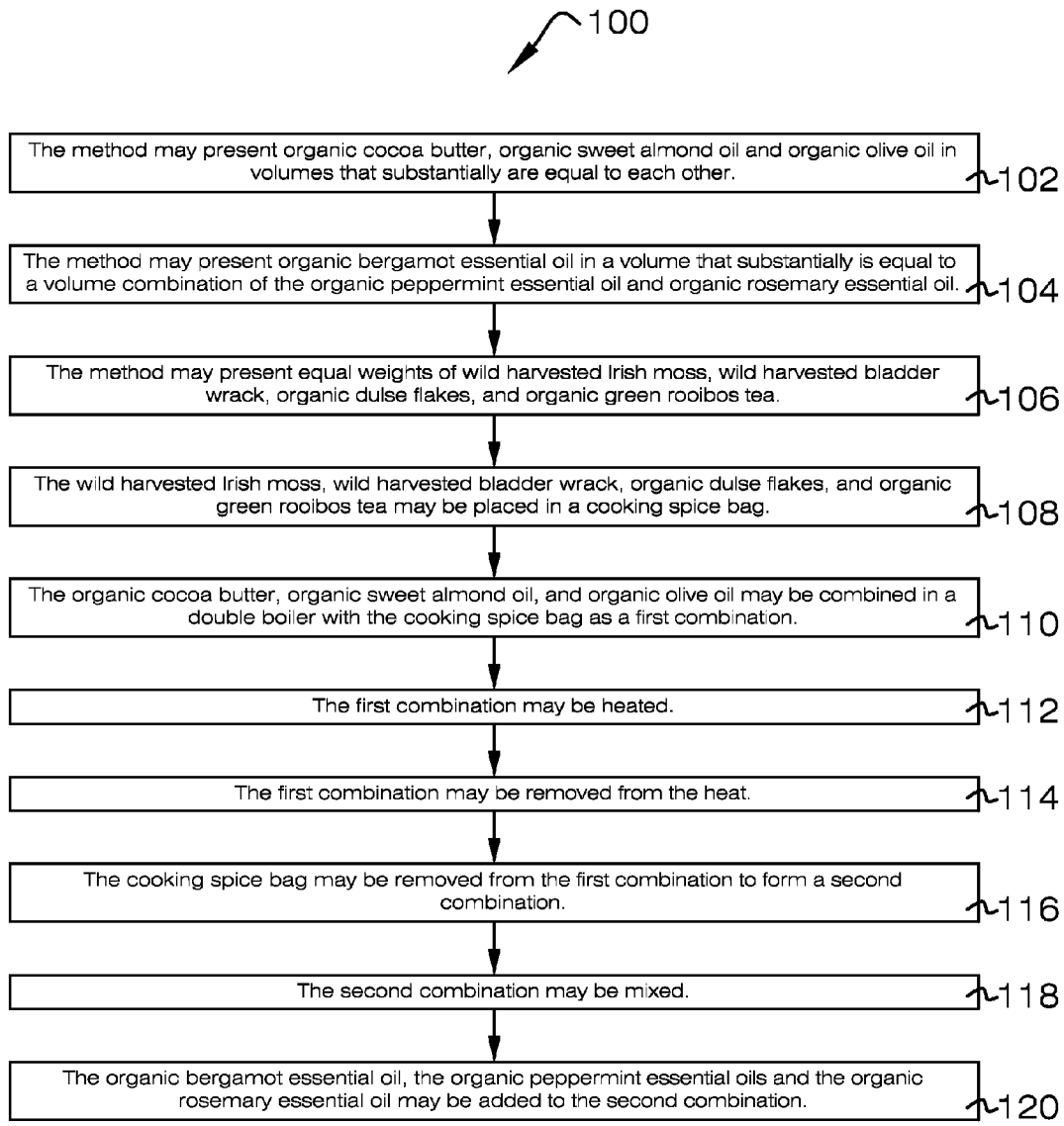
FIG. 1 is a method 100 to produce a hand and body skincare cream composition.

The composition may be an oil-based hand and body emollient composed of organically grown ingredients. When combined, the ingredients may form an all-natural cream that may assist in moisturize and revitalize human skin. Some of the ingredients may be added directly as part of the composition while other items may undergo a process to extract ingredients for the composition.

The composition may include organic cocoa butter, organic sweet almond oil, and organic olive oil that may provide bulk to the composition, organic peppermint, organic rosemary, and organic bergamot as essential oils, and extracts drawn from wild harvested Irish moss, wild harvested bladder wrack, organic dulse, and organic green rooibos tea. The composition additionally may include preservatives.

For those ingredients that may be organic, they may be produced according to legally regulated organic standards set by the country in which they are sold. For example, the organic ingredients of the composition may be grown and manufactured in a manner that adheres to standards set by National Organic Program (NOP) Standards in the United States, Organic Farmers and Growers Organic Standards in Britain, NASAA Organic Standard in Australia, and JAS Standards in Japan. This may include growing the items without the use of conventional pesticides, artificial fertilizers, sewage sludge, and genetically modified organisms as well as processing the items without ionizing radiation or food additives.

For those ingredients that may be wild harvested, they may be gathered from locations where they may exist in naturally, rather than through cultivation. Also, they may be gathered according to legally regulated wild harvest standards set by the country in which they may be gathered. For example, the wild harvested ingredients of the composition may be gathered in a manner that adheres to standards set by National Organic Program (NOP) Standards in the United States, Organic Farmers and Growers Organic Standards in Britain, NASAA Organic Standard in Australia, and JAS Standards in Japan. This may include gathering or harvesting the ingredients from a predestinated area that has been free from conventional pesticides and other prohibited substances for at least three years. The actual harvesting or gathering of the wild crop should not be destructive to the environment and should sustain the growth and production of the wild crop. Once harvested, the crop producer should not add prohibited substances to the wild crop by.

Cocoa butter may be the creamy, rich fat obtained from the seeds of the cocoa plant. It may be refined to remove cocoa odors. In the composition, the cocoa butter may serve as a rich emollient to soften the skin with a soothing sensation.

Sweet almond (*Prunus dulcis*) oil may be oil drawn from almonds after soaking the almonds with a sweetener and grounding and/or mashing the soaked raw almonds. The sweet almond oil may provide rich, fatty acids to the composition.

Olive oil (*olca europaca*) may be a vegetable oil obtained from pressing tree-ripened olives (*Olea europaea*). Olive oil may help maintain adequate moisture in the skin by slowing the loss of water through the skin layers. In the composition, the olive oil may serve as an ideal skin conditioner.

Essential oils may be aromatic liquid substances that may be extracted from certain species of flowers, grasses, fruits, leaves, roots, and trees. Generally, the peppermint, rosemary, and bergamot may provide aromatherapy as well as a refreshing sensation. Peppermint (*mentha piperita*) essential oil may be oil from the peppermint plant that may help a user of the composition to clear their mind as well as provide anti-inflammatory effects to the skin and relaxation to the muscles under the skin. Rosemary (*rosmarinus officinalis*) essential oil may be oil extracted from the woody, perennial herb of the same name and may affect joint pain and poor circulation positively. Bergamot (*citrus bergamia*) essential oil may be oil obtained from the bergamot orange and may help ward off skin infections.

Natural essences of plant matter may be obtained through techniques such as expression, absorption by steeping, maceration, and distillation. The extract ingredients of the composition generally may be obtained by soaking particular plant matter to draw out ingredients and having the extraction absorbed into the composition. As noted above, the extract ingredients may include Irish moss, bladder wrack (sometimes spelled bladderwrack), and dulse.

Irish moss (*chondrus crispus*) is a species of red algae that may contribute Irish moss iodine, calcium, magnesium, and potassium nutrients to the composition to benefit human nails and skin hair follicles. Bladder wrack (*fucus vesiculosus*) is seaweed that may contribute bladder wrack alginic acid to the composition to help reduce swelling. Dulse (*palmaria palmata* (L.) *kuntze*) is a red alga (*rhodophyta*) that may contribute dulse phytochemicals, minerals, and iodine to the composition. The dulse may be made into flakes by cutting dried dulse leafs into small flakes Green rooibos tea includes leaves from the rooibos flowering shrub (*aspalathus linearis*) that may be dried to prevent oxidation and retain polyphenol antioxidants such that the green rooibos tea may contribute rooibos antioxidants to the composition.

As noted above, the composition may include preservatives. The preservatives may extend a shelf life of the composition to greater than two years by retarding spoilage that may result from microbial growth and/or undesirable chemical changes. In one example, the preservative may be a combination of diazolidinyl urea and iodopropynyl butylcarbamate solubilized in propylene glycol to ward against bacteria, yeast, and mold. In another example, the preservative may be Liquid Germal® Plus. In addition to preservatives, the composition additionally may include, for example, stabilizers, humectants, surfactants, detergent additives, other skincare additives, thickeners, emulsifiers, self-tanning additives, perfumes, dyes, other antioxidants, additional vitamins, ultra violate filters, water, and silicone oils.

The composition may include organic cocoa butter, organic sweet almond oil, and organic olive oil, where the organic cocoa butter, organic sweet almond oil, and organic olive oil each may exist in the composition in volumes that substantially may be equal to each other. The composition additionally may include organic bergamot essential oil, organic peppermint essential oil, and organic rosemary essential oil, where the organic bergamot essential oil may exist in the composition in a volume that substantially may be equal to a volume combination of the organic peppermint and rosemary essential oils. Further, the composition may include extracts drawn from equal parts by weight of wild harvested Irish moss, wild harvested bladder wrack, organic dulse flakes, and organic green rooibos tea.

Example No. 1

A hand and body skincare cream composition having the following composition was prepared:
  extract from 56.5 grams wild harvested Irish moss
  extract from 56.5 grams wild harvested bladder wrack
  extract from 56.5 grams organic dulse flakes
  extract from 56.5 grams organic green rooibos tea
  120 milliliters (½ cup) organic cocoa butter
  120 milliliters (½ cup) organic sweet almond oil
  120 milliliters (½ cup) organic olive oil
  4 drops (21 microliters; $\frac{1}{15}$ of a teaspoon) organic peppermint essential oil
  4 drops (21 microliters; $\frac{1}{15}$ of a teaspoon) organic rosemary essential oil
  8 drops (10 microliters; $\frac{2}{15}$ of a teaspoon) organic bergamot essential oil
  720 milligrams Liquid Germal® Plus The following method was utilized to prepare the hand and body skincare cream composition of Example No. 1.

The wild harvested Irish moss, wild harvested bladder wrack, organic dulse flakes, and organic green rooibos tea were placed into individual cooking spice bags. The organic cocoa butter, sweet almond oil, and olive oil were combined in a double boiler with the individual cooking spice bags. This combination was heated until the organic cocoa butter had melted completely. The organic cocoa butter melted combination then was removed from heat to cool.

At a point where the organic cocoa butter melted combination began to gel, the individual cooking spice bags were removed from the combination. The remaining combination was permitted to cool for a predetermined amount of time. After the allotted time had expired, a hand mixer was used, first on low speed for a predetermined amount of time and then high speed to until the combination reached a whipped state. The organic peppermint, rosemary, and bergamot essential oils then were first mixed with the Liquid Germal® Plus and this mixture was then folded into the whipped combination for a predetermined amount of time.

FIG. 1 is a method 100 to produce a hand and body skincare cream composition. At step 102, the method may present organic cocoa butter, organic sweet almond oil, and organic olive oil in volumes that substantially are equal to each other. At step 104, the method may present organic bergamot essential oil in a volume that substantially is equal to a volume combination of the organic peppermint essential oil and organic rosemary essential oil. Moreover, at step 106, the method may present equal weights of wild harvested Irish moss, wild harvested bladder wrack, organic dulse flakes, and organic green rooibos tea.

At step 108, the wild harvested Irish moss, wild harvested bladder wrack, organic dulse flakes, and organic green rooibos tea may be paced in a cooking spice bag. At step 110, the organic cocoa butter, organic sweet almond oil, and organic olive oil may be combined in a double boiler with the cooking spice bag as a first combination.

The term double boiler may include any two containers that may be configured to be nested so that the contents of the upper container may be cooked slowly and evenly by boiling a liquid in the lower container may be utilized. The liquid in the lower container may be water or other liquid. At step 112, the first combination may be heated.

At step 114, the first combination may be removed from the heat. At step 116, the cooking spice bag may be removed from the first combination to form a second combination. At step 118, the second combination may be mixed. At step 120, the organic bergamot essential oil, the organic peppermint essential oil, and the organic rosemary essential oil may be added to the second combination.

The hand and body skincare cream composition may be an oil based hand and body emollient having organically grown and wild crafted ingredients. The ingredients may be edible and the composition may contain natural essential oils that may contribute fragrance.

The composition may be applied after bathing to soften and nourish the skin. In addition to helping a user's skin regain resiliency, the composition may help keep the skin soft and moist. The composition may provide the user with healthy and attractive skin and a more even complexion. The composition may be packaged in a jar, offered in a wide variety of sizes and scents, and used on a daily basis.

The composition may fulfill a need for a specially formulated cream that may leave a person's skin soft, moist, fresh, and attractive. Appealing features of the composition may be its all-natural ingredients, novel formula, convenience, ease of use, effectiveness, versatility, light weight, compact size, and portability. The composition may gently soften and moisturize a person's skin from shower to shower and may provide him/her with healthier skin.

The composition may be particularly appealing to individuals with skin conditions, such as dry skin, eczema, and rashes. This composition also may appeal to individuals who frequently wash their hands on a daily basis, such as doctors, dentists, and cooks. The composition may rejuvenate the skin for a younger, healthier appearance. The composition may be formulated from all-natural ingredients and may offer nutritional benefits. The composition may contain all natural, essential oils, which may be a healthier alternative to creams with artificial ingredients. The composition may be affordably priced, versatile, convenient, effective, and fragrant. In addition, a lightweight and compact package may be stored and transported easily while traveling. For those allergic to seaweed, other plant extracts may be utilized to create a similar composition.

The compositions disclosed in this patent may be prepared in any desired manner and in any suitable order or sequence of addition of the various components and those skilled in the art may be readily cognizant of those available mixing procedures that may be operative for ease and speed of production of such compositions.

The information disclosed herein is provided merely to illustrate principles and should not be construed as limiting the scope of the subject matter of the terms of the claims. The written specification and figures are, accordingly, to be regarded in an illustrative rather than a restrictive sense. Moreover, the principles disclosed may be applied to achieve the advantages described herein and to achieve other advantages or to satisfy other objectives, as well.

What is claimed is:

1. A hand and body skincare cream composition, comprising components:
    a) organic cocoa butter;
    b) organic sweet almond oil;
    c) organic olive oil;
    d) organic bergamot essential oil;
    e) organic peppermint essential oil;
    f) organic rosemary essential oil;
    g) extracts from equal parts by weight of wild harvested Irish moss, wild harvested bladder wrack, organic dulse flakes, and organic green rooibos tea; and
    h) a preservative that is configured to extend a shelf life of the composition to greater than two years, wherein the preservative comprises diazolidinyl urea and iodopropynyl butylcarbamate solubilized in propylene glycol;
    wherein components a), b) and c) have substantially equal volumes; and the extracts are produced by soaking wild harvested Irish moss, wild harvested bladder wrack, organic dulse flakes, and organic green rooibos tea in a mixture of components a), b) and c); and
    wherein component d) has a volume that is substantially equal to the combination volume of components e) and f).

2. The hand and body skincare cream composition of claim 1, where the composition includes 120 milliliters organic cocoa butter, 120 milliliters organic sweet almond oil, and 120 milliliters organic olive oil.

3. The hand and body skincare cream composition of claim 2, where the composition includes eight drops of organic bergamot essential oil, four drops of organic peppermint essential oil, and four drops of organic rosemary essential oil.

4. The hand and body skincare cream composition of claim 3, where the extracts are drawn produced from 56.5 grams wild harvested Irish moss, 56.5 grams wild harvested bladder wrack, 56.5 grams organic dulse flakes, and 56.5 grams organic green rooibos tea.

* * * * *